United States Patent [19]
Weier

[11] Patent Number: 5,762,615
[45] Date of Patent: Jun. 9, 1998

[54] GUIDEWARE HAVING A DISTAL TIP WITH VARIABLE FLEXIBILITY

[75] Inventor: Steven D. Weier, Miramar, Fla.

[73] Assignee: Cordis Corporation, Miami, Fla.

[21] Appl. No.: 658,680

[22] Filed: Jun. 4, 1996

[51] Int. Cl.⁶ ........................................................ A61B 5/00
[52] U.S. Cl. ............................................. 600/585; 604/284
[58] Field of Search ..................................... 128/772, 657, 128/658; 604/95, 280–282

[56] References Cited

U.S. PATENT DOCUMENTS

| | | | |
|---|---|---|---|
| 3,547,103 | 12/1970 | Cook | 604/95 |
| 3,854,473 | 12/1974 | Matsuo . | |
| 4,215,703 | 8/1980 | Willson . | |
| 4,757,827 | 7/1988 | Buchbinder et al. | 128/772 |
| 4,815,478 | 3/1989 | Buchbinder et al. . | |
| 4,846,186 | 7/1989 | Box et al. . | |
| 4,886,067 | 12/1989 | Palermo . | |
| 4,917,102 | 4/1990 | Miller et al. . | |
| 4,922,924 | 5/1990 | Gambale et al. | 128/772 |
| 4,940,062 | 7/1990 | Hampton et al. . | |
| 5,238,005 | 8/1993 | Imran . | |
| 5,267,574 | 12/1993 | Viera et al. . | |
| 5,370,109 | 12/1994 | Cuny | 604/281 |
| 5,480,382 | 1/1996 | Hammerslag et al. . | |

FOREIGN PATENT DOCUMENTS

| | | |
|---|---|---|
| 486157 | 5/1992 | European Pat. Off. . |
| 92/14508 | 9/1992 | European Pat. Off. . |
| 4130042 | 3/1993 | Germany . |

*Primary Examiner*—Max Hindenburg
*Assistant Examiner*—Pamela L. Wingood
*Attorney, Agent, or Firm*—Dean L. Garner

[57] ABSTRACT

In accordance with the present invention, there is provided a guidewire for navigating through body vessels so as to deliver a balloon catheter or the like. The guidewire has an elongated core wire having distal and proximal ends and a longitudinal axis extending therebetween. The guidewire also has a coiled spring surrounding the distal end of the core wire. Lastly, the guidewire includes a tube surrounding the core wire proximal to the coiled spring. The tube is able to slide back and forth with respect to the longitudinal axis of the core wire. The tube has a distal end and a proximal end. The distal end of the tube is coupled the proximal end of the coil so that as the tube slides along the longitudinal axis of the core wire, the length of the coiled spring changes, thereby changing the flexibility of the coil.

8 Claims, 1 Drawing Sheet

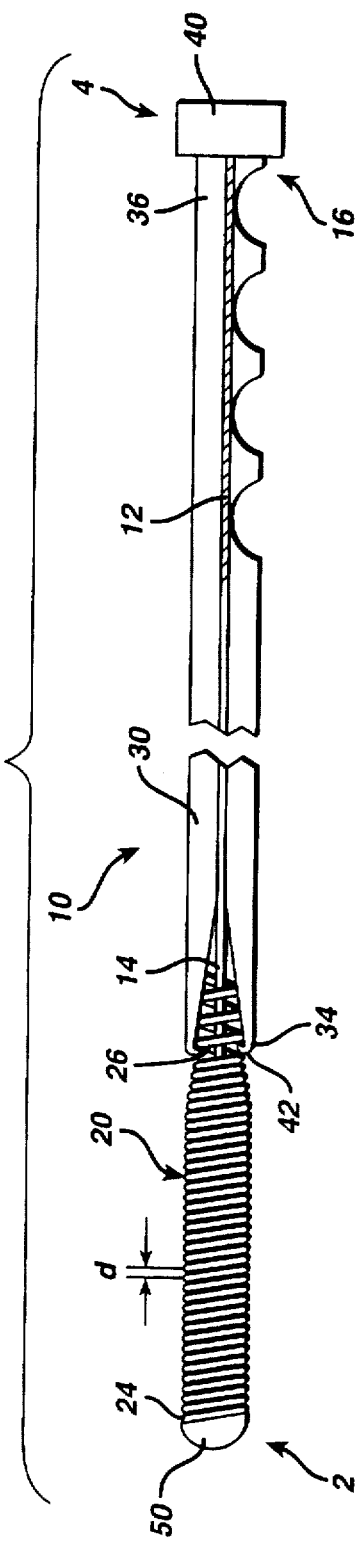
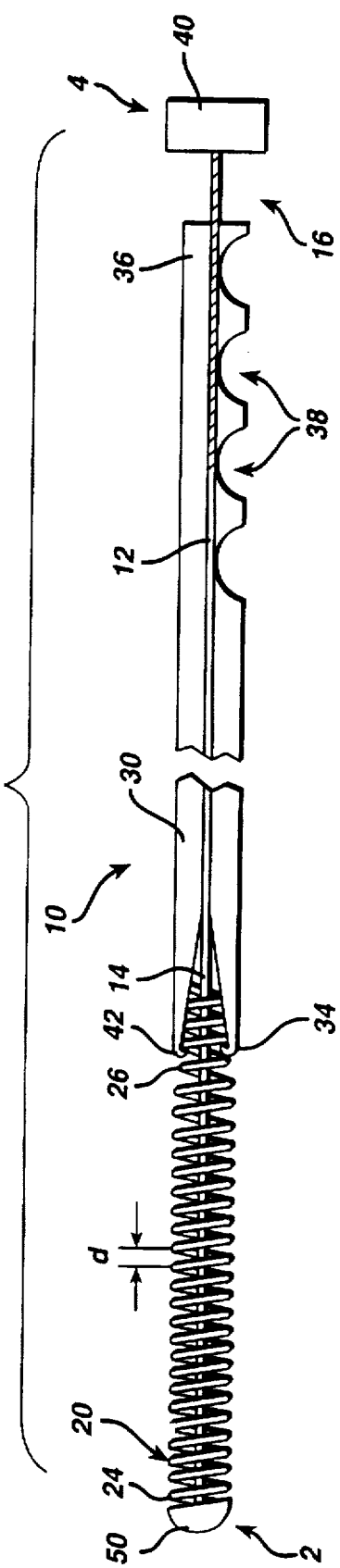

GUIDEWARE HAVING A DISTAL TIP WITH VARIABLE FLEXIBILITY

FIELD OF THE INVENTION

The present invention relates to a flexible elongated guidewires used in medical procedures. The present invention has further relation to such a guidewire which is used to position a catheter, such as a balloon catheter, within a patient.

BACKGROUND OF THE INVENTION

Percutaneous transluminal coronary angioplasty is a therapeutic medical procedure used to increase blood flow through the coronary artery and can often be used as an alternative to coronary by-pass surgery. An elongated catheter having a deflated balloon at its distal end is guided through a patient's cardiovascular system to the coronary artery of the heart. The balloon is inflated to compress deposits that have accumulated along the inner walls of the coronary artery to widen the artery lumen and increase blood flow. Typically, the balloon catheter is guided to the specific area within the vessel by an elongated guidewire. The guidewire is inserted into the patient and routed through the cardiovascular system and can be viewed on an x-ray imaging screen.

The path the guidewire follows during this procedure is often tortuous. The distal tip of the guidewire is flexible to avoid damaging inner walls of the blood vessels that the guidewire tip contacts along the tortuous path. The distal tip is often pre-bent to a desired configuration so that the guidewire can be inserted into branching blood vessels along its path. When the tip is pre-bent, the physician must be able to orient the tip so it can be pushed into these branching blood vessels. Examples of prior art guidewires are shown in U.S. Pat. 4,846,186 issued to Box et al. on Jul. 11, 1989 and U.S. Pat. 5,267,574 issued to Viera et al. on Dec. 7, 1993, both of which are hereby incorporated herein by reference.

Such guidewires typically have a core made from stainless steel or the like and coated with a lubricity enhancing agent, such as Teflon ®. The distal end of the guidewire is not coated as such and usually comprises one or two tapered portions which reduce the diameter of the core wire at its distal end. The distal most portion of the core wire is then flattened to form a ribbon tip which makes it easier for a physician to form into a desired shape. A flexible coiled wire spring surrounds the distal tip of the core wire and is attached thereto. The coil separates from the core wire for a predetermined length and is attached proximal to the flattened distal portion of the core wire.

Various prior art guidewires often range in the flexibility of their distal tips. Often it is preferable to have an extremely floppy tip, because it can better navigate very tortuous paths. However, a more stiff distal tip is better able to force its way through lesions/occlusions.

There has, therefore, been a desire to provide a guidewire having a tip that can change its flexibility. There has also been a desire to provide such a guidewire wherein the physician can easily and quickly change the flexibility of the tip. The present invention provides such a guidewire.

SUMMARY OF THE INVENTION

In accordance with the present invention, there is provided a guidewire for navigating through body vessels so as to deliver a balloon catheter or the like. The guidewire has an elongated core wire having distal and proximal ends and a longitudinal axis extending therebetween. The guidewire also has a coiled spring surrounding the distal end of the core wire. Lastly, the guidewire includes a tube surrounding the core wire proximal to the coiled spring. The tube is able to slide back and forth with respect to the longitudinal axis of the core wire. The tube has a distal end and a proximal end. The distal end of the tube is coupled the proximal end of the coil so that as the tube slides along the longitudinal axis of the core wire, the length of the coiled spring changes, thereby changing the flexibility of the coil.

BRIEF DESCRIPTION OF THE DRAWINGS

While the specification concludes with claims which particularly point out and distinctly claim the subject matter forming the present invention, it is believed that the invention will be better understood from the following description taken in conjunction with the accompanying drawings wherein:

FIG. 1 is a simplified enlarged partial-sectional view of the guidewire of the present invention.

FIG. 2 is a view similar to that of FIG. 1 but showing the coil in a longer more flexible state.

DETAILED DESCRIPTION OF THE INVENTION

Turning now to the drawings in detail, wherein like numerals indicate the same element throughout the views, there is shown in FIGS. 1 and 2 a guidewire 10 in accordance with the present invention. Guidewire 10 has a distal end 2 and a proximal end 4. Guidewire 10 is preferably long enough to be routed from a patient entry point through the patient to the obstructed blood vessel region. In a preferred embodiment the guidewire has a length of 175 cm. (approximately 69 inches). Guidewire 10 has an elongated core wire 12 with a distal end 14 and a proximal end 16 and a longitudinal axis extending therebetween. Core wire 12 can be made from stainless steel or any other suitable material such as Nitinol. Guidewire 10 also has a coiled spring 20 surrounding distal end 14 of core wire 12. Coiled spring 20 has a distal end 24 and a proximal end 26. The distal end 4 of guidewire 10 includes a weld 50 or other means of attachment such as soldering or brazing which attaches the spring 20 to the core wire. The weld, braze or solder 50 defines a smooth hemispherical bead that does not damage the inner lining of the blood vessels as the guidewire tip comes in contact with those linings.

Distal end 6 of the guidewire 10 is flexible and preferably can be bent to a predetermined configuration to facilitate routing the guidewire 10 along body vessels. The pre-bent tip can be re-oriented by the physician. Torques applied to the proximal end 4 of the guidewire are transmitted along the length of the guidewire and re-orient the distal tip to point in a desired direction. For angioplasty, the distal end 2 of the guidewire 10 is routed through narrow and tortuous passageways until it reaches and crosses an obstruction or lesion. Thereafter, a balloon catheter is slipped over the guidewire until it reaches the obstructions within a blood vessel. The balloon is then inflated and the balloon's outer surface contacts the obstruction. The inner walls of the obstruction are compressed and a wider lumen or passageway created in the blood vessel.

Guidewire 10 further includes a sliding means for changing the flexibility of the coiled spring 20 of guidewire 10. In FIGS. 1 and 2 this sliding means is a tube 30 surrounding core wire 12 proximal to coiled spring 20. Tube 30 can be made from any number of suitable materials including polyamide, and can be coated with Teflon or the like to enhance its lubricity. Tube 30 has a distal end 34 and a proximal end 36. Distal end 34 of tube 30 is coupled to proximal end 26 of the coil 20. Tube 30 is capable sliding back and forth along the longitudinal axis of core wire 12 so that the length of coiled spring 20 can be changed. By sliding tube 30 away from distal end 14 of core wire 10, the spring will lengthen, as shown in FIG. 2, so as to increase the distance d between adjacent coils. This makes the spring more flexible. By sliding the tube towards distal end 14, the spring will shorten, as shown in FIG. 1, so as to decrease the distance d between adjacent coils. This makes the spring less flexible. A stop 40 is connected to the distal end 16 of core wire 12 to prevent the spring from over stretching and detaching from the rest of the guidewire. Friction between the tube and core wire can keep the spring in position.

Tube 30 has a number of sections 38 cut away at its proximal end 36. This allows the physician fingers to touch core wire 12, allowing him to manipulate the tip flexibility at will and enable him to feel the tip of the wire touch the vessel.

Distal end 34 of tube 30 is attached to the spring by a downwardly extending annular flange 42. However, the tube can be attached to the spring by any suitable means known in the art.

The diameter of the spring 20 tapers from a diameter at its distal end which is equal to the diameter of the tube 30 (0.009–0.038 inch) to a diameter at its proximal end which is slightly larger than the diameter of the core wire (0.009–0.038 inch). A preferred spring is formed of coiled platinum wire having a wire diameter of 0.002 to 0.003 inches. The platinum wire is radiopaque and therefore the spring 20 forms a visible band under fluoroscopy. As the sliding means or tube 30 changes the length of spring 20, it would also change the degree of radiopacity of the coil 20. As the spring stretches, it becomes less visible and vise-versa.

The guidewire may have a number of radiopaque marker bands (not shown) placed along its length. The marker bands are preferably platinum rings that are commercially available. The rings are placed at the distal end 2 of the guidewire, proximal to the spring 20.

Although particular embodiments of the present invention have been shown and described, modification may be made to the catheter without departing from the spirit and scope of the present invention. The terms used in describing the invention are used in their descriptive sense and not as terms of limitations.

What is claimed is:

1. A guidewire for navigating through body vessels, said guidewire having distal and proximal ends, said guidewire comprising:

(a) an elongated core wire having distal and proximal ends, and a longitudinal axis extending therebetween;

(b) a coiled spring surrounding said distal end of said core wire, said spring having distal and proximal ends and a length extending therebetween, said distal end of said spring being attached to said core wire, said core wire extending through said spring, said distal end of said guidewire having the ability to be manually bent to a desired configuration prior to insertion into said body vessels; and (c) a tube surrounding said core wire proximal to said distal end of said coiled spring, said tube being able to slide back and forth with respect to said longitudinal axis of said core wire without being rotated, said tube having a distal end and a proximal end, said distal end of said tube being coupled to said coil such that as said tube slides along said longitudinal axis of said core wire with the angular position of said tube with respect to said longitudinal axis remaining substantially constant, the length of said coiled spring changes.

2. The guidewire according to claim 1 wherein said tube includes a number of cut out sections at its proximal end so as to expose said core wire.

3. The guidewire according to claim 1 wherein said proximal end of said core wire extends proximally of said tube.

4. The guidewire according to claim 3, wherein said core wire includes a stop at its proximal end, said stop being proximal of said tube and having an outer diameter at least equal to that of said tube.

5. The guidewire according to claim 1 further including a means for preventing said spring from overstretching.

6. The guidewire according to claim 1 wherein said guidewire has a smooth hemispherical bead at its distal most tip.

7. The guidewire according to claim 6 wherein said distal end of said coiled spring is attached to said smooth hemispherical bead.

8. The guidewire according to claim 7 wherein said coiled spring is radiopaque.

* * * * *